United States Patent [19]

Lawter et al.

[11] Patent Number: 5,000,886

[45] Date of Patent: Mar. 19, 1991

[54] SILICONE-HARDENED PHARMACEUTICAL MICROCAPSULES AND PROCESS OF MAKING THE SAME

[75] Inventors: James R. Lawter, Goshen; Michael G. Lanzilotti, Pearl River, both of N.Y.

[73] Assignee: American Cyanamid COmpany, Stamford, Conn.

[21] Appl. No.: 54,372

[22] Filed: May 26, 1987

[51] Int. Cl.$^5$ .............................................. A61K 9/50
[52] U.S. Cl. ...................... 264/4.3; 264/4.6; 427/213.32; 427/213.36; 514/963; 424/460
[58] Field of Search ................. 264/4.3, 4.6; 427/213.32, 213.36; 514/963; 424/460

[56] References Cited

U.S. PATENT DOCUMENTS

| | | | |
|---|---|---|---|
| 4,107,071 | 8/1978 | Bayless | 252/316 |
| 4,107,072 | 8/1978 | Morse et al. | 252/316 |
| 4,389,330 | 6/1983 | Tice et al. | 427/213.36 |
| 4,675,189 | 6/1987 | Kent et al. | 514/963 X |
| 4,732,763 | 3/1988 | Beck et al. | 514/932 X |
| 4,877,561 | 10/1989 | Iga et al. | 264/4.3 |

FOREIGN PATENT DOCUMENTS

| | | |
|---|---|---|
| 0052510 | 5/1982 | European Pat. Off. |
| 0092918 | 11/1983 | European Pat. Off. |
| 0058481 | 10/1986 | European Pat. Off. |
| 2034182 | 6/1980 | United Kingdom |

OTHER PUBLICATIONS

Lee R. Beck & Valerie Z. Pope, Controlled-Release Delivery Systems for Hormones A Review of their Properties & Current Therapeutic Use, Department of Obstetrics & Gynecology, Div. of Reproductive Biology & Endocrinology, Drugs 27: pp. 528–547 (1984).

R. G. Gupta & B. C. Rao, Microencapsulation of Vitamin B-12 by Emulsion Technique, Drug Development & Industrial Pharmacy, 11(1), 41–53 (1985).

S. Benita, J. P. Benoit, F. Puisieux and C. Thies, Characterization of Drug-Loaded Poly(d,1-lactide) Microspheres, Journal of Pharmaceutical Sciences/ pp. 1721–1724, vol. 73, No. 12, Dec., 1984.

Lee R. Beck, Ph.D., Donald R. Cowsar, Ph.D. & Valerie Z. Pope, M.S., Research Frontiers In Fertility Regulation, AID/DSPE-C-0035, pp. 1–17, vol. 1, No. 1, Jul. 1980.

*Primary Examiner*—Robert L. Stoll
*Assistant Examiner*—Gary L. Geist
*Attorney, Agent, or Firm*—H. G. Jackson

[57] ABSTRACT

There is disclosed a process for preparing compositions comprising microcapsules by phase separation microencapsulation wherein the hardening agent employed is a volatile silicone fluid and with the compositions prepared thereby. The use of the volatile silicone fluid as a hardening agent permits the production of microcapsules substantially free of any alkane hardening agent, eliminating potential combustability problems of the prior art processes and toxicity problems of the prior art compositions.

36 Claims, No Drawings

SILICONE-HARDENED PHARMACEUTICAL MICROCAPSULES AND PROCESS OF MAKING THE SAME

This invention is concerned with a process for preparing compositions comprising microencapsulated pharmaceutical agents by phase separation microencapsulation, wherein the hardening agent is a volatile silicone fluid and with compositions prepared thereby.

BACKGROUND OF THE INVENTION

Microcapsules consist of a core material surrounded by a coating or encapsulating substance which is normally a polymer. Microcapsules may consist of one or more spherical core particles surrounded by a coating, or the microencapsulated substance may exist as one or more irregularly shaped particles surrounded by a coating which may have spherical form, or the exterior of the microcapsules may be irregular in shape. In general, microcapsules are produced to provide protection for the core material and/or to control the rate of release of the core material to the surrounding environment. Also included within the term microcapsule are those in which the pharmaceutical agent is present as a solid solution in the coating and may be present at one or more points or portions of the microcapsule surface. The term microsphere has also been applied to the above-named microcapsules.

As suggested by Beck et al., U.S. Pat. No. 4,585,651, dated Apr. 29, 1986 which discloses pharmaceutical compositions comprising microparticles of a pharmaceutical agent incorporated in a biocompatible and biodegradable matrix material, the methods for preparation of microcapsules may be classified in three principal types:

(1) phase separation methods including aqueous and organic phase separation processes, melt dispersion and spray drying;

(2) interfacial reactions including interfacial polymerization, in situ polymerization and chemical vapor depositions; and (3) physical methods, including fluidized bed spray coating, electrostatic coating and physical vapor deposition.

The distinguishing feature of phase separation microencapsulation is the initial production of a new dispersed phase containing the coating substance via some physical or chemical change. The dispersed coating phase ultimately surrounds and coats the core material which itself is also initially dispersed or dissolved in the continuous phase.

In one preferred type of phase separation, microencapsulation is carried out by addition of a non-solvent for the coating polymer and the core material to a solution of the coating polymer which contains dispersed or dissolved core material. This type of phase separation process comprises the following steps.

(i) A solution of coating material is prepared.

(ii) The core material is dispersed or dissolved in the coating solution. The core material may be solid or liquid and may or may not be soluble in the coating solution. The core material may also contain, in addition to any pharmaceutical agent, excipients such as antioxidants, preservatives, release-modifying agents, and the like. Any or all of the core material ingredients may be solid or liquid.

(iii) While stirring the composition of (ii), a non-solvent for the coating material and core material is added. The non-solvent must be miscible with or soluble in the coating solvent. Addition of the non-solvent causes the coating material to come out of solution in the form of a dispersed liquid phase comprising a concentrated solution of the coating polymer in the original coating solvent. In the case where the core material is soluble in the coating solution, the core material will also be present in the coating solution phase. In the case where the core material is not soluble in the coating solution, the newly created phase surrounds and coats the dispersed core phase. In this instance, a necessary property of the coating phase is that it wet the core phase in preference to the continuous phase.

(iv) The dispersion (iii) is added to the hardening solvent. The purpose of this solvent is to extract polymer solvent from the coating/core droplets formed in step (iii). After hardening, the microcapsules will exist as particles suspended in the hardening solvent. The microcapsules may then be recovered by filtration or other convenient means.

Kent et al., European Patent Publication Number EPO-052- 510, published May 26, 1982, discloses the microencapsulation of water soluble polypeptides in biocompatible, biodegradable polymers such as poly(-lactide-co-glycolide)copolymers, also by a phase separation process utilizing an alkane solvent, and specifically exemplifies heptane as a hardening solvent.

The previously used hardening agents including hexane, heptane, cyclohexane and other alkane solvents leave substantial amounts of hardening agent residues in the microcapsules. Tests have shown that heptane hardened microcapsules typically contain 5–15% by weight of heptane. Since hardening agents can ultimately be released, low toxicity is of paramount importance for hardening agents used to produce microcapsules for pharmaceutical applications, and it would be advantageous to provide the same.

In addition, a further drawback in use of hydrocarbon hardening agents of the prior art is that they are flammable and therefore require the use of explosion-proof facilities for manufacturing microcapsules.

It has now been discovered that if volatile silicone fluids are used as hardening agents, the drawbacks of the prior art are overcome because of their very low toxicity and non-flammability characteristics. Microcapsules produced by the phase separation microencapsulation process are different and better than those of the prior art because the residual hardening agent content is very low, e.g., of the order of less than 2–3 wt %, preferably less than 1–2% and more preferably less than 1%. The results obtained herein are surprising because, while the coating material solvent is readily removable by vacuum drying, it has heretofore been the experience that residual prior art hardening agents, once incorporated into microcapsules, are not readily removed by drying because they are, by nature, not soluble in the coating material and therefore do not permeate through the coating material.

Volatile silicone fluids are unique because these fluids essentially are not incorporated into the microcapsules during the hardening step.

The improvement in phase separation microencapsulation thus provided by the present invention removes a major obstacle which in the past has prevented use of this technology to produce a drug delivery system.

SUMMARY OF THE INVENTION

In accordance with the present invention, there is provided an improvement in a known process for preparing a pharmaceutical composition in microcapsule form, said process comprising:

(a) dispersing a solution containing a pharmaceutical agent in an organic solvent containing a biocompatible encapsulating polymer which may also be biodegradable;

(b) adding to the dispersion a non-solvent for the encapsulating polymer and pharmaceutical agent; and (c) adding the product of step (b) to a hardening solvent to extract said organic solvent and produce solid microcapsules of said pharmaceutical composition, the improvement comprising using as the hardening solvent a volatile fluid.

Also provided by the invention are compositions of matter comprising a microencapsulated core material wherein the microcapsules are prepared by phase separation microencapsulation employing a volatile silicone fluid as a hardening agent. Such compositions are different from those of the prior art because they have a residual hardening agent content of less than about 3% by weight, preferably less than 2% by weight and especially preferably less than 1% by weight and are substantially free of any alkane hardening agents.

Criteria which core materials must satisfy in order to be microencapsulated by the process of this invention are as follows. The core material must have low solubility in the coating non-solvent and also low solubility in the volatile silicone hardening agent. Low solubility means less than about 5% weight/weight; preferably less than about 1% and most preferably less than about 0.1%. Also in the case of core materials which are microencapsulated as solids or liquids dispersed in the coating solution, the concentrated coating solution phase generated upon addition of the non-solvent must wet the core phase in preference to the continuous phase. In the case of core materials which are soluble in the initial coating solution, the core material must partition into the coating phase generated upon addition of the coating non-solvent. Thus the class of core materials which may be microencapsulated by the process of this invention is determined by the physicochemical properties of the core, coating, coating solvent and hardening agent.

Among the pharmaceutical agents which satisfy these criteria in general are peptides and proteins. Specific examples of the latter are: atrial natriuretic factor, tumor necrosis factor, oxytocin, vasopressin, adrenocorticotrophic hormone (ACTH), epidermal growth factor, tryocidins, gramicidins, gramicidins, renin, bradykinin, angiotensins, enctorphins, enkephalins, calcitonin, salmon calcitonin, secretin, calcitonin gene related factor, tissue plasminogen factor, kidney plasminogen factor, cholecystokinin, melanocyte inhibiting factor, melanocyte stimulating hormone, neuropeptide y, nerve growth factor, muramyl dipeptide, thymopoietin, human growth hormone, porcine growth hormone, bovine growth hormone, insulin, thyrotropin releasing hormone (TRH), arogastrone, pentagastrin, tetragastrin, gastrin, interferons, glucagon, somatostatin, prolactin, superoxide dismutose, luteinizing hormone releasing hormone (LHRH), H-5-Oxo-Pro-His-Trp-Ser-Tyr-DTrp-Leu-Arg-Pro-GlyNH$_2$, H-5-Oxo-Pro-His-Trp-Ser-Tyr-3-(2 Napthyl)-D-alanyl-Leu-Arg-Pro-Gly-NH$_2$, Luteinizing hormone-releasing factor (pig), 6-[0-(1,1-dimethylethyl)-D-serine]-10-deglycinamide-, 2-(aminocarbonyl)hydrazide (9CI), Luteinizing hormone-releasing factor (pig), 6-[0-(1,1-dimethylethyl)-D-serine]-9-(N-ethyl-L-prolinamide)-10-deglycinamide- (9CI), Luteinizing hormone-releasing factor (pig), 6-D-leucine-9-(N-ethyl-L-prolinamide)-10-deglycinamide- (9CI) and synthetic analogs and modifications and pharmacologically active fragments thereof and pharmaceutically acceptable salts thereof.

Other classes of compounds suitable for microencapsulation by this process includes: penicillins, beta-lactamase inhibitors, cephalosporine, quinolones, aminoglycoside antibiotics (gentamicin, tobramycin, kanamycin, amikacin), estradiol, norethisterone, norethindrone, progesterone, testosterone, amcinonide, achromycin, tetracyclines (doxycycline, minocycline, oxytetracycline, tetracycline, chlortetracycline, demeclocycline, methacyline), clindamycin, Vitamin B-12, anesthetics (procaine, tetracaine, lidocaine, mepivacaine, etidocaine), mitoxantrone, bisantrene, doxorubicin, mitomycin C, bleomycin, vinblastine, vincristine, cytosine arabinoside, ARA-AC, actinomycin D, daunomycin, daunomycin benzoylhydrazone, nitrogen mustards, 5-azacytidine, calcium leucovorin, cis-platinum compounds, 5-fluorouracil, methotrexate, aminopterin, maytansine, melphalan, mecaptopurines, methyl CCNU, hexamethylmelamine, etoposide, hydroxyurea, levamisole, mitoquazone, misonidazole, pentostatin, teniposide, thioquanine, dichloromethotrexate, chloprothixene, molindone, loxapine, haloperidol, chlorpromazine, triflupromazine, mesoridazine, thioridazine, fluphenazine, perphenazine, trifluoperazine, thiothixene, and pharmaceutically acceptable salts of the foregoing, hydromorphone, oxymorphone, levorphenol, hydrocodone, oxycodone, nalorphine, naloxone, naltrexone, buprenorphine, butorphenol, nalbuphine, mepridine, alphaprodine, anileridine, diphenoxylate, fentanyl and pharmaceutically acceptable salts of the foregoing.

The encapsulating polymer may be biodegradable or non-biodegradable as the application dictates. The term biodegradable is used herein to mean that the polymer degrades when administered to a living organism by hydrolysis or as a result of enzymatically catalyzed degradation or by a combination of the two.

Among the encapsulating polymers which can be utilized, there are named: polyglycolide, polylactide (L OR DL), poly(glycolide-co-l-lactide), poly(glycolide-co-dl-lactide), poly(p-dioxanone), poly(glycolide-co-trimethylene carbonate), poly(alkylene diglycolates), poly(alkylene succinates), poly(alkylene oxalates), poly(capro-lactone), poly(-hydroxybutyric acid), poly(ortho esters), poly(anhydrides), poly(amide-esters), poly(alkylene tartrate), poly(alkylene fumarate), cellulose based polyurethanes, ethyl cellulose, methyl cellulose, hydroxypropyl cellulose, and other cellulose derivatives.

In addition, blends of the above polymers and other copolymers of the above may be used.

The choice of non-solvent is dictated by the chemical nature of the encapsulation polymer and the polymer solvent. The non-solvent must be miscible with the polymer solvent and as the name implies, a non-solvent for the encapsulating polymer or coating. The non-solvent must have greater affinity for the polymer solvent than the encapsulating polymer. Typical non-solvents are silicone oils (polydidemethylsiloxane), vegetable oils, polyisobutylene, mineral oils, cyclic polydimethylsiloxanes and related oils and the like.

Encapsulating polymer or coating solvents must be miscible with the hardening agent which in the process of this invention is a volatile silicone fluid. Typically, halogenated organic solvents such as methylene chloride and 1,1,2-trichloroethane or other $C_1$-$C_4$ halogenated alkanes are employed.

The volatile silicone fluid is preferably octamethylcyclotetrasiloxane or decamethylcyclopentasiloxane or a low molecular weight linear polydimethylsiloxane, such as hexamethyldisiloxane.

DETAILED DESCRIPTION OF THE INVENTION

The methods and materials used to prepare microencapsulated pharmaceutical agents are well known to those skilled in the art as evidenced by the above-mentioned patents and publications.

Merely by way of illustration, biodegradable polymers such as poly(glycolide-co-dl-lactide), poly(lactide) and other similar polyester type polymers have been used to produce microcapsules containing a number of drugs. The solvent used for these polymers is normally methylene chloride or other halogenated solvents, such as $C_1$-$C_4$ halogenated alkanes, e.g., methylene chloride and 1,1,2-trichloroethane. Phase inducing substances, i.e., non-solvents, or the so-called coacervation agents, are typically silicone oil (polydimethylsiloxane), vegetable oils and polyisobutylene, but they can also include mineral oils, and other related oils, and the like. The hardening solvents most commonly used in the prior art are flammable alkanes such as heptane and cyclohexane.

It is essential in the current invention to use a particular class of hardening agents for phase separation microencapsulation induced by the addition of a non-solvent for the coating polymer.

These hardening agents are volatile silicone fluids.

Suitable volatile silicone fluids are:
octamethylcyclotetrasiloxane;
decamethylcyclopentasiloxane; and
low molecular weight linear polydimethylsiloxanes such as hexamethyldisiloxane.

Preferred agents are octamethylcyclotetrasiloxane and decamethylcyclopentasiloxane. These agents are non-flammable (flash points of 55° C. and 76° C., respectively). Also, since they are pure substances rather than mixtures, they may be easily recovered by distillation and recycled.

Such fluids can be made by procedures known to those skilled in this art; and they are all commercially available.

The microcapsules may range in diameter from about 0.1 to 1000 microns, preferably 5 to 200 microns, and especially preferably 10–180 microns, depending on the procedure employed. They may be administered to a subject by any means or route desired. The amount of pharmaceutical agent used will comprise an effective amount greater than a conventional single dose. This can be readily determined by those skilled in this art, but, for example, if a hormone is used, the amount will comprise up to about 70% by weight of the microcapsules, preferably from about 0.01 to about 40% by weight of the microcapsules, and especially preferably from 0.1 to 10% by weight of the microcapsules.

While the composition of matter employing the above described hardening agents and the process by which the microcapsules are produced are generically applicable to a variety of pharmaceutical agents, they are specifically applicable to microcapsule formulations containing peptides or proteins such as those listed above.

For example, (D-Trp$^6$)-LH-RH, a synthetic decapeptide analogue of the naturally occurring Luteinizing Hormone Releasing Hormone, used for the treatment of hormone related diseases such as hormone-dependent breast, prostate and ovarian cancers, endometriosis and precocious puberty.

One of the main problems with this product is that it must be administered parenterally and because it has a short biological half-life daily injection is required which is at best inconvenient and has undesirable effects.

Microcapsules prepared with a biodegradable encapsulating polymer according to the current invention provide the ideal delivery system for D-Trp$^6$-LH-RH and related or similar drugs. Injected subcutaneously or intramuscularly, the polymer portion of the microcapsule will biodegrade and bioerode, resulting in the release of the peptide into the body for periods ranging from several hours to several months.

DESCRIPTION OF THE PREFERRED EMBODIMENTS

The following examples illustrate the invention, but are not intended to limit the claims in any manner whatsoever.

EXAMPLE 1

A 6.0 g portion of poly(glycotide-co-dl-lactide) polymer was added to 300 g of methylene chloride and dissolved by stirring at high speed for 24 hours. A 0.24 g portion of D-Trp$^6$-LH-RH ® (84% purity) was added to approximately one half of the polymer/methylene chloride solution and was dispersed with a homogenizer.

The drug/polymer/methylene chloride solution together with the remainder of the polymer-methylene chloride solution was then added to a vessel equipped with a stirrer rotating at 2250 rpm. This mixture was stirred until homogeneous and a non-solvent consisting of 218 g of polydimethyl siloxane having a viscosity of 350 centistokes was infused into the mixture at a rate of 4 ml per minute. The total mixing time was 56 minutes.

This mixture was then discharged into 6 gallons of octamethylcyclotetrasiloxane and mixed at a speed of 750 rpm. When the microspheres were completely discharged into the octamethylcyclotetrasiloxane the mixing speed was increased to 1500 rpm. The total mixing time was 2.5 hours.

The hardened microcapsules were collected by passing the mixture through a stainless steel collection screen having 5 micron openings. The microcapsules were then vacuum dried.

The above microcapsules were tested to determine the rate of D-Trp$^6$-LH-RH release in vitro by the following procedure:

The release apparatus consisted of a porous microcapsule container which was placed in a culture tube containing a specified amount of the release medium, pH 7.4 phosphate buffer. The tube was rotated in a 37° C. incubator. Periodically over a period of 45 days the release medium was removed, assayed for D-Trp$^6$-LH-RH by HPLC, and replaced with fresh medium.

Drug release was observed to occur over a period of forty-five days.

Residual octamethylcyclotetrasiloxane levels were found to be two to three percent by weight. For comparison, heptane hardened microcapsules contain 5-15% heptane typically.

EXAMPLE 2

If the procedure of Example 1 is repeated, substituting decamethylcyclopentasiloxane for octamethylcyclotetrasiloxane, substantially the same results will be obtained.

EXAMPLE 3

If the procedure of Example 1 is repeated, substituting hexamethyldisiloxane for octamethylcyclotetrasiloxane, substantially the same results will be obtained.

EXAMPLE 4

A 50 gram batch of D-Trp$^6$-LH-RH microcapsules was produced using the following method:

A 50 gram portion poly(glycolide-co-lactide) having a lactide to glycolide rates of approximately 53:47 and an inherent viscosity of about 0.65 dl/g (as measured in a 0.5% w/v hexafluoroisopropanol solution at 30° C.) copolymer was dissolved into 950 grams methylene chloride by stirring overnight. The solution was filtered through a stainless steel screen having eight micron openings.

An amount of 2.0 grams of spray-dried D-Trp$^6$-LH-RH was mixed into the polymer solution using high shear mixer for about 30 seconds. The D-Trp$^6$-LH-RH had a mean particle size of approximately 3 microns.

The drug/copolymer/methylene chloride solution was added to the microencapsulation vessel equipped with a stirrer rotating at 300 rpm. A non-solvent consisting of 1,000 grams of a polydimethylsiloxane having a viscosity of 350 centistokes was infused at 100 grams/min. The total mixing time was 12 minutes. This mixture was then discharged into 5 gallons (18.2 kilos) of octamethylcyclotetrasiloxane and mixed at 750 rpm. When the microspheres were completely discharged the mixing speed was increased up to 1500 rpm. Total mixing time was 2 hours.

The hardened microcapsules were then collected by passing the mixture through a stainless steel screen with eight micron openings. The microcapsules were then vacuum dried.

EXAMPLE 5

A six gram batch of cyanocobalamin (Vitamin B$_{12}$) microcapsules were produced using the following method:

120 grams of a 5% (w/w) poly(glycolide-co-dl-lactide) polymer solution in methylene chloride was filtered through a 0.2 micron millipore membrane filter. The polymer had an inherent viscosity of about 0.29 dl/g (as measured in a 0.5 w/v hexafluoroisopropanol solution at 30° C.) and a lactide to glycolide ratio of about 53:47.

An amount of 0.24 grams Vitamin B$_{12}$ having a mean particle size of about 5 microns was added to the 120 grams of filtered 5% solution. The B$_{12}$ was blended into the polymer solution using a homogenizer for about 30 seconds.

The B$_{12}$ solution was added to the microencapsulation vessel equipped with a stirrer rotating at 300 rpm. A non-solvent consisting of polydimethylsiloxane having a viscosity of 350 centistokes was infused at 100 grams per minute for one minute to give a total added quantity of 100 grams. The solution was stirred for an additional two minutes.

The above suspension was discharged into 4 gallons of octamethylcyclotetrasiloxane fluid mixed for 2 hours at a stirrer speed increased over time from 750 to 1500 rpm.

Microcapsules were collected, rinsed with octamethylcyclotetrasiloxane and dried under vacuum. The microcapsules ranged in diameter from about 30 to 120 microns.

EXAMPLE 6

A 15 gram batch of minocycline microspheres was produced using the following method:

A 300 gram portion of a 5% poly(glycolide-co-dl-lactide) solution in methylene chloride was filtered through a 0.2 micron millipore membrane. The polymer had an inherent viscosity of about 0.67 dl/g (as determined in a 0.5% (w/v) hexafluoroisopropanol solution at 30° C.) and a lactide to glycolide ratio of about 53:47.

A 6.2 gram portion of micronized minocycline HCL (85.7% pure and having a mean particle size of about 3 microns) was added to the 300 grams of filtered polymer solution.

The drug was dispersed in the polymer solution with a homogenizer for about 1 to 2 minutes.

The suspension was added to a microencapsulation vessel equipped with a stirrer and stirring at 300 rpm. Polydimethylsiloxane having a viscosity of 350 centistokes was infused at 100 grams per minute for 3 minutes for a total of 300 grams. The mixture was stirred for an additional 2 minutes then discharged into 5 gallons of octamethylcyclotetrasiloxane mixing at speeds varying from 750 rpm to 1500 rpm for two hours.

The microcapsules were collected by filtration, rinsed with octamethylcyclotetrasiloxane and dried under vacuum. Diameters of these microcapsules ranged from about 30 to 120 microns.

The above-mentioned patents and publications are incorporated herein by reference.

Many variations of this invention will occur to those skilled in this art in light of the above, detailed description. For example, instead of (D-Trp$^6$)-LH-RH, a steroid hormone can be used, e.g., norethindrone, norethisterone, and the like or other vitamins or antibiotics can be used. Instead of silicone oil as a non-solvent, mineral oil or peanut oil can be used. All such obvious variations are within the full intended scope of the appended claims.

We claim:

1. In a process for preparing a pharmaceutical composition in microcapsule form, said process comprising:
   (a) dispersing a solution containing a core material which is comprised of a pharmaceutical agent in an organic solvent containing a biocompatible encapsulating polymer, which core material has low solubility in the non-solvent of step (b) and the hardening agent of step (c);
   (b) adding to the dispersion a non-solvent for the encapsulating polymer and core material, which non-solvent is miscible with the organic solvent and in which the core material has a low solubility; and
   (c) adding the product of step (b) to a hardening solvent to extract said organic solvent and produce solid microcapsules of said pharmaceutical composition, the improvement which comprises using as the hardening solvent a volatile silicone fluid.

2. In a process for preparing a pharmaceutical composition in microcapsule form, said process comprising:
   (a) dispersing a core material comprising solid particles comprised of a pharmaceutical agent in a solution of a biocompatible encapsulating polymer in an organic solvent in which the core material has a low solubility;
   (b) stirring the dispersion produced in (a) while adding a non-solvent for said encapsulating polymer and said core material, said non-solvent being soluble in said organic solvent whereby the encapsulating polymer separates from solution as a liquid phase consisting essentially of a concentrated solution of the encapsulating polymer in said organic solvent and selectively coats the core material particles; and
   (c) adding the coated core particle dispersion from step (b) to a hardening agent to extract said organic solvent and produce solid microcapsules of said pharmaceutical composition, the improvement comprising utilizing as the hardening agent a volatile silicone fluid in which the core material has low solubility.

3. A process as defined in claim 1 wherein the non-solvent for the encapsulating polymer is a second polymer incompatible with said encapsulating polymer.

4. A process as defined in claim 2 wherein the non-solvent for the encapsulating polymer is a second polymer incompatible with said encapsulating polymer.

5. A process as defined in claim 1 wherein the biocompatible encapsulating polymer is also biodegradable.

6. A process as defined in claim 2 wherein the biocompatible encapsulating polymer is also biodegradable.

7. A process as defined in claim 1 wherein said core material comprises a vitamin or an antibiotic.

8. A process as in claim 7 wherein said vitamin is vitamin B-12.

9. A process as in claim 7 wherein the antibiotic is selected from the group consisting of tetracycline, doxycycline, minocycline, methacycline, declomycin, oxytetracycline, and chlortetracycline or the pharmaceutically acceptable salts thereof.

10. A process as in claim 7 wherein the antibiotic is a cephalosporin.

11. A process as in claim 7 wherein the antibiotic is a penicillin.

12. A process as in claim 7 wherein the antibiotic is a quinolone.

13. A process as in claim 7 wherein the antibiotic is an aminoglycoside.

14. A process as in claim 1 wherein the core material is comprised of a mixture of a penicillin antibiotic and a beta-lactamose inhibitor.

15. A process as defined in claim 1 wherein the core material comprises a peptide or pharmaceutically acceptable salt thereof.

16. A process as defined in claim 15 wherein the peptide is a luteinizing hormone releasing hormone analog or a pharmaceutically acceptable salt thereof.

17. A process as defined in claim 16 wherein the luteinizing hormone releasing hormone analog is D-Trp$^6$-LH-RH or a pharmaceutically acceptable salt thereof.

18. A process as defined in claim 16 wherein the luteinizing hormone releasing hormone analog is (pyro)Glu-His-Trp-Ser-Tyr-3-Napthyl-D-Alanyl-Leu-Arg-Pro-Gly-NH$_2$ or a pharmaceutically acceptable salt thereof.

19. A process as defined in claim 1 wherein the core material comprises a protein or pharmaceutically acceptable salt thereof.

20. A process as defined in claim 1 wherein the core material comprises an anesthetic.

21. A process as defined in claim 20 wherein the anesthetic is selected from the group consisting of procaine, lidocaine, tetracaine and etidocaine or a pharmaceutically acceptable salt thereof.

22. A process as defined in claim 1 wherein the organic solvent comprises methylene chloride.

23. A process as defined in claim 1 wherein the encapsulating polymer comprises a polymer of lactic acid or a copolymer of lactic acid and glycolic acid.

24. A process as defined in claim 23 wherein said polymer comprises dl-lactide-co-glycolide copolymer.

25. A process as defined in claim 1 wherein said non-solvent in step (b) comprises a silicone oil, a volatile silicone fluid, a mineral oil, a vegetable oil or a mixture of any of the foregoing.

26. A process as defined in claim 11 wherein said non-solvent comprises a silicone oil.

27. A process as defined in claim 26 wherein said non-solvent comprises a polydimethylsiloxane fluid.

28. A process as defined in claim 1 wherein said volatile silicone fluid comprises octamethylcyclotetrasiloxane, decamethylcyclopentasiloxane or a low molecular weight polydimethylsiloxane.

29. A process as defined in claim 28, wherein said volatile silicone fluid comprises octamethylcyclotetrasiloxane.

30. A process as defined in claim 1 wherein the solubility of the core material in the non-solvent is less than about 5% weight/weight.

31. A process as defined in claim 1 wherein the solubility of the core material in the non-solvent is less than about 1% weight/weight.

32. A process as defined in claim 1 wherein the solubility of the core material in the non-solvent is less than about 0.1% weight/weight.

33. A process as defined in claim 1 wherein the volatile silicone fluid is miscible with the encapsulating polymer solvent.

34. In a process of preparing a composition in microcapsule form by phase separation microencapsulation, the improvement comprising employing a hardening agent comprising a volatile silicone fluid.

35. A process according to claim 34 in which the volatile silicone fluid comprises octamethylcyclotetrasiloxane, decamethylcyclopentasiloxane or a low molecular weight polydimethylsiloxane.

36. A process according to claim 35 in which the volatile silicone fluid comprises octamethylcyclotetrasiloxane.

* * * * *